(12) United States Patent
Gibson et al.

(10) Patent No.: US 11,045,655 B2
(45) Date of Patent: *Jun. 29, 2021

(54) FIXATION SYSTEM FOR AN IMPLANTABLE MEDICAL DEVICE

(71) Applicant: Cochlear Limited, Macquarie University (AU)

(72) Inventors: Peter Gibson, South Coogee (AU); Lars Vendelbo Johansen, Aarhus (DK)

(73) Assignee: Cochlear Limited, Macquarie University (AU)

( * ) Notice: Subject to any disclaimer, the term of this patent is extended or adjusted under 35 U.S.C. 154(b) by 249 days.

This patent is subject to a terminal disclaimer.

(21) Appl. No.: 15/852,779

(22) Filed: Dec. 22, 2017

(65) Prior Publication Data

US 2018/0169416 A1 Jun. 21, 2018

Related U.S. Application Data

(63) Continuation of application No. 15/406,190, filed on Jan. 13, 2017, now Pat. No. 10,610,691, which is a
(Continued)

(30) Foreign Application Priority Data

Aug. 9, 2002 (AU) .................. 2002950755

(51) Int. Cl.
*A61N 1/37* (2006.01)
*A61N 1/375* (2006.01)
(Continued)

(52) U.S. Cl.
CPC ..... *A61N 1/37518* (2017.08); *A61N 1/36036* (2017.08); *A61N 1/375* (2013.01);
(Continued)

(58) Field of Classification Search
CPC .............. A61N 1/0541; A61N 1/36036; A61N 1/36038; A61N 1/375
See application file for complete search history.

(56) References Cited

U.S. PATENT DOCUMENTS 2,487,038 A 11/1949 Baum
2,641,328 A 6/1953 Beaudry
(Continued)

FOREIGN PATENT DOCUMENTS

RU 2282426 C1 8/2006
WO 8300999 A1 3/1983
(Continued)

OTHER PUBLICATIONS

International Preliminary Examination Report for PCT/AU2003/000229, dated May 2004.
(Continued)

*Primary Examiner* — Eric D. Bertram
(74) *Attorney, Agent, or Firm* — Pilloff Passino & Cosenza LLP; Martin J. Cosenza

(57) ABSTRACT

A medical implant, such as an implantable component (22) of a tissue-stimulating prosthesis. One example of such a prosthesis being a cochlear implant. The component (22) is adapted to be implanted at or adjacent a tissue surface within the recipient, such as a bone surface. The component (22) has a housing and at least one flange (42) extending outwardly therefrom. The flange (42) can be secured to the tissue surface via a tissue fixation device, such as a bone screw (43).

40 Claims, 10 Drawing Sheets

Related U.S. Application Data continuation of application No. 10/523,800, filed as application No. PCT/AU03/01004 on Aug. 8, 2003, now Pat. No. 9,545,522.

(51) Int. Cl.
   *A61N 1/36* (2006.01)
   *A61N 1/372* (2006.01)
   *A61F 11/00* (2006.01)

(52) U.S. Cl.
   CPC ........ *A61N 1/37223* (2013.01); *A61F 11/004* (2013.01); *A61F 2220/0008* (2013.01)

(56) References Cited

U.S. PATENT DOCUMENTS

| | | | |
|---|---|---|---|
| 3,768,977 | A | 10/1973 | Brumfield et al. |
| 4,055,233 | A | 10/1977 | Huntress |
| 4,333,469 | A | 6/1982 | Jeffcoat et al. |
| 4,488,561 | A | 12/1984 | Doring |
| 4,532,930 | A | 8/1985 | Crosby et al. |
| 4,590,946 | A | 5/1986 | Loeb |
| 4,612,915 | A | 9/1986 | Hough et al. |
| 4,744,792 | A | 5/1988 | Sander et al. |
| 4,904,233 | A | 2/1990 | Hakansson et al. |
| 4,986,831 | A | 1/1991 | King et al. |
| 5,176,620 | A | 1/1993 | Gilman |
| 5,277,694 | A | 1/1994 | Leysieffer et al. |
| 5,282,253 | A | 1/1994 | Konomi |
| 5,443,493 | A | 8/1995 | Byers et al. |
| 5,558,618 | A | 9/1996 | Maniglia |
| 5,572,594 | A | 11/1996 | Devoe et al. |
| 5,738,521 | A | 4/1998 | Dugot |
| 5,814,095 | A | 9/1998 | Muller et al. |
| 5,881,158 | A | 3/1999 | Lesinski et al. |
| 5,906,635 | A | 5/1999 | Maniglia |
| 5,999,632 | A | 12/1999 | Leysieffer et al. |
| 6,042,380 | A | 3/2000 | De Rowe |
| 6,070,105 | A | 5/2000 | Kuzma |
| 6,125,302 | A | 9/2000 | Kuzma |
| 6,132,384 | A | 10/2000 | Christopherson et al. |
| 6,161,046 | A | 12/2000 | Maniglia et al. |
| 6,293,903 | B1 | 9/2001 | Kasic, II et al. |
| 6,381,336 | B1 | 4/2002 | Lesinski et al. |
| 6,427,086 | B1 | 7/2002 | Fischell et al. |
| 6,516,228 | B1 | 2/2003 | Berrang et al. |
| 6,537,200 | B2 | 3/2003 | Leysieffer et al. |
| 6,565,503 | B2 | 5/2003 | Leysieffer et al. |
| 6,575,894 | B2 | 6/2003 | Leysieffer et al. |
| 6,618,623 | B1 * | 9/2003 | Pless ............... A61N 1/375 607/116 |
| 6,697,674 | B2 | 2/2004 | Leysieffer |
| 6,730,015 | B2 | 5/2004 | Schugt et al. |
| 6,840,919 | B1 | 1/2005 | Hakansson |
| 7,043,040 | B2 | 5/2006 | Westerkull |
| 7,937,156 | B2 | 5/2011 | Gibson |
| 7,974,700 | B1 | 7/2011 | Gibson |
| 9,545,522 | B2 * | 1/2017 | Gibson ............ A61N 1/36036 |
| 10,610,691 | B2 * | 4/2020 | Gibson ............ A61N 1/37223 |
| 2002/0019669 | A1 | 2/2002 | Berrang et al. |
| 2002/0091419 | A1 * | 7/2002 | Firlik ............... A61N 1/37514 607/45 |
| 2002/0138115 | A1 | 9/2002 | Baumann |
| 2004/0260361 | A1 | 12/2004 | Gibson |
| 2006/0030852 | A1 | 2/2006 | Sevrain |
| 2006/0116743 | A1 | 6/2006 | Gibson et al. |
| 2009/0099658 | A1 | 4/2009 | Dalton et al. |
| 2011/0160855 | A1 | 6/2011 | Gibson |
| 2011/0208303 | A1 | 8/2011 | Gibson |
| 2011/0264170 | A1 | 10/2011 | Gibson |

FOREIGN PATENT DOCUMENTS

| | | |
|---|---|---|
| WO | 3429932 A1 | 12/1994 |
| WO | 9705673 A1 | 2/1997 |
| WO | 9436457 A1 | 10/1997 |
| WO | 9906108 A1 | 2/1999 |
| WO | 0071063 A1 | 11/2000 |
| WO | 0110369 A1 | 2/2001 |
| WO | 03070133 A1 | 8/2003 |
| WO | 03092326 A1 | 11/2003 |
| WO | 2004014269 A1 | 2/2004 |
| WO | 2004014270 A1 | 2/2004 |
| WO | 2007053882 A1 | 5/2007 |
| WO | 2009099658 A2 | 8/2009 |

OTHER PUBLICATIONS

International Preliminary Examination Report for PCT/AU2000/000936, dated Jun. 2001.
International Search Report for PCT/AU2000/000936, dated Oct. 10, 2000.
International Search Report for PCT/AU2003/000229, dated May 5, 2003.
Written Opinion for PCT/AU2003/00229, dated Jun. 30, 2003.
International Search Report for PCT/AU03/01004, dated Oct. 13, 2003.
International Preliminary Examination Report for PCT/AU03/01004, dated Nov. 2004.
International Search Report for PCT/AU03/001012, dated Oct. 13, 2003.
International Preliminary Examination Report for PCT/AU03/001012, dated Nov. 2004.
Written Opinion for PCT/AU03/01004, dated Jan. 9, 2006.
Written Opinion for PCT/AU03/001012, dated Feb. 23, 2004.
Gerald A. Niznick, "Achieving Osseointegration in Soft Bone: The Search for Improved Results," Oral Health, Aug. 2000, pp. 27-32.
International Search Report for PCT/AU2006/001632, dated Dec. 1, 2006.
Written Opinion for PCT/AU2006/001632, dated Dec. 1, 2006.
International Preliminary Report on Patentability for PCT/AU2006/001632, dated May 14, 2008.

* cited by examiner

FIXATION SYSTEM FOR AN IMPLANTABLE MEDICAL DEVICE

The present application is a Continuation application of U.S. patent application Ser. No. 15/406,190, filed Jan. 13, 2017, now U.S. Pat. No. 10,610,691, naming Peter Gibson as an inventor, which is a Continuation application of U.S. patent application Ser. No. 10/523,800, filed Nov. 3, 2005, now U.S. Pat. No. 9,545,522, which is a National Stage of PCT/AU03/01004, filed Aug. 8, 2003, which claims priority to AU Application No. 2002950755, filed Aug. 9, 2002. The entire contents of these applications are incorporated herein by reference in their entirety.

FIELD OF THE INVENTION

The present invention resides in an improved method of mounting an implantable component of an implantable medial device, such as a cochlear implant package, securely in the head region of a recipient.

BACKGROUND OF THE INVENTION

In many people who are profoundly deaf, the reason for deafness is absence of, or destruction of, the hair cells in the cochlea which transduce acoustic signals into nerve impulses. These people are unable to derive suitable benefit from conventional hearing aid systems, no matter how loud the acoustic stimulus is made, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve.

Cochlear implant systems have typically consisted of essentially two components, an external component commonly referred to as a processor unit and an internal implanted component commonly referred to as a receiver/stimulator unit. Traditionally, both of these components have cooperated together to provide the sound sensation to a user.

The external component has traditionally consisted of a microphone for detecting sounds, such as speech and environmental sounds, a speech processor that converts the detected sounds, particularly speech, into a coded signal, a power source such as a battery, and an external transmitter antenna coil.

The coded signal output by the speech processor is transmitted transcutaneously to the implanted receiver/stimulator unit situated within a recess of the temporal bone of the user. This transcutaneous transmission occurs via the external transmitter antenna coil which is positioned to communicate with an implanted receiver antenna coil provided with the receiver/stimulator unit.

This communication serves two essential purposes, firstly to transcutaneously transmit the coded sound signal and secondly to provide power to the implanted receiver/stimulator unit. Conventionally, this link has been in the form of a radio frequency (RF) link, but other such links have been proposed and implemented with varying degrees of success.

The implanted receiver/stimulator unit traditionally includes a receiver antenna coil that receives the coded signal and power from the external processor component, and a stimulator that processes the coded signal and outputs a stimulation signal to an intracochlear electrode assembly which applies the electrical stimulation directly to the auditory nerve producing a hearing sensation corresponding to the original detected sound.

Traditional implanted receiver/stimulator units are positioned within the head of the recipient by drilling a bed into and through the posterior section of the mastoid bone lying behind the recipient's ear. Such a bed is usually made by drilling the bone down to the lining of the brain or dura mater, so that the receiver/stimulator unit is maintained in position and does not protrude excessively past the skull surface.

The receiver/stimulator unit manufactured by the present Applicant has a package made from titanium which houses the stimulation electronics and which is fitted into a bed created in the mastoid bone. A receiver antenna coil extends from the rear end of the package and lies superficial to the bone. Other cochlear implants have included packages made from a ceramic material which are usually placed completely within the bed drilled down to the dura mater.

Various techniques have been implemented in order to mount or fix the device in place and to ensure that the device does not undergo movement once implanted.

One such technique has been to drill holes in the bone surrounding the device and to use sutures or Dacron ties to hold the device in place. One problem with this approach is that drilling of the holes into the surrounding bone can be a difficult and time consuming procedure, and especially for young children, much care must be taken by the surgeon to ensure that the drilling does not perforate the dura mater, as the skull thickness in such cases can be quite thin. Further to this, the suture or Dacron ties may not be sufficiently strong enough to withstand a substantial impact to a region of the head adjacent the device and as a result, such a force may dislodge the device from its desired position. In addition, it has been found that if a suture or Dacron tie is inadvertently placed across an inappropriate section of the device, such as across a strain relief of the electrode lead, the suture/tie may cause the lead/device to undergo fatigue and cause failure at this location.

Another technique used to secure the implant device in place is for the surgeon to craft a suitable well or bed in the cranial bone that is capable of maintaining the device in place without the need of sutures or ties. Such a technique relies upon the shape of the well or bed being such that the surrounding bone can hold the device in place. This technique is not always possible depending upon the thickness of the surrounding bone and the age and anatomy of the recipient.

Therefore, there is a need to provide a fixation method for an implantable hearing prosthesis that is capable of securely maintaining the device in place in a desired region of the recipient's head without the need for additional sutures or ties.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention is a medical implant for implantation within a body of a recipient, the medical implant comprising a hermetically sealed housing, said housing having at least one flange extending outwardly therefrom that is securable to tissue within the body of the recipient.

In this aspect, the flange can be securable to a suitable tissue surface. While a bone surface is preferred, it can be envisaged that the flange could be securable to a other suitable tissues within the body, including cartilage and tendons.

In one embodiment, the implant can be an implantable component of a tissue-stimulating prosthesis. In a preferred embodiment, the tissue-stimulating prosthesis is a cochlear implant. The implantable component of the cochlear implant preferably comprises a receiver/stimulator package of such an implant. While the present application will hereinafter refer to cochlear implants, it is to be understood that the invention has a potential wider application to other implantable tissue-stimulating prostheses.

In one embodiment, the housing of the implantable component can be adapted to be placed on the surface of the bone of the recipient. In the case of a cochlear implant, this bone would likely be the mastoid bone. In another embodiment, a bed or well can be formed in the surface of the bone, such as the mastoid bone, such that the housing can be positioned in the well or bed.

In one embodiment, a flange can extend outwardly from the housing in at least one direction. More preferably, the housing has at least two flanges extending outwardly therefrom. In this embodiment, the flanges preferably extend in substantially opposite directions relative to each other. In a further embodiment where there are two flanges, the respective flanges can extend in opposite directions relative to each other.

In one embodiment, at least one flange preferably extends from a first or upper surface of the housing. The first surface of the housing is preferably the outer surface of the housing on implantation of the component.

In another embodiment, at least one flange can extend from a second or lower surface of the housing. In this embodiment, the second surface preferably faces inwardly, such that the surface normally abuts with or is embedded in the bone of the recipient receiving the implantable component.

In a still further embodiment, at least one flange can extend from the housing at a location between the first and second surfaces of the housing. In one embodiment, the flange can extend outwardly from a location that is approximately midway between the first and second surfaces.

In yet another embodiment and where there is more than one flange, one of such flanges may extend from the first or upper surface while another extends from the second or lower surface. Other flange combinations can be envisaged.

In a further embodiment, the flanges extending from the housing comprise part of a plate mounted to the housing of the implantable component. In one embodiment, the plate can be removably or non-removably mounted to the housing.

Each of the flanges are preferably adapted to abut the tissue surface of the recipient following implantation of the implantable component. In one embodiment, the flanges are preferably conformable to the tissue surface. In this regard, the flanges can be formed from a malleable material that allows the flanges to be conformed to the surface of the tissue, such as bone. In another embodiment, the flanges can be constructed so as to be conformable to the tissue surface. In this regard, the flanges may have a thickness that allows the flanges to be suitably conformable during the surgical procedure. In a still further embodiment, both the properties of the material and the construction of the flanges may play a role in ensuring the flanges are malleable and conformable to the tissue surface. The flanges are preferably conformable by finger pressure exertable on the flanges by a surgeon during the surgical implant of the implantable component.

The degree of conformation of the flanges necessary to ensure the flanges conform to the tissue surface will depend on the position of the flanges and/or whether the housing of the component is embedded within the tissue, such as within a well or bed within the bone. Where the flanges extend from the first surface of the housing, the downward angle of the flanges necessary so as to abut with the tissue surface will depend on the degree to which the housing is embedded within the tissue. The downward angle of the flange is likely to be less when the housing is at least partially embedded in the tissue in comparison to the situation where the housing essentially is sitting on the tissue surface.

In one embodiment, the flanges can have a thickness between about 0.1 mm and 0.3 mm. The flanges can be formed from a malleable material.

In one embodiment, the flanges can constitute an integral extension of the housing of the implantable component. In another embodiment, the flanges can be formed separately and mounted to the housing. Techniques such as welding and brazing can be envisaged as techniques for mounting the flanges to the housing of the implantable component. In another embodiment, one or more flanges may be an integral extension of the housing while one or more may be formed separately and mounted to the housing.

In another embodiment, the flanges can be removably mounted to the housing. In this embodiment, the flanges or housing of the implantable component can be provided with engagement means adapted to engage with the housing or flanges, respectively. In one embodiment, the housing can have one or more clips adapted to engage with the flanges. In this embodiment, it is envisaged that the flanges may not be mounted to the housing until surgery is underway and the size and shape of the flanges required for that particular surgery have been determined. Still further, removably mounted flanges provide the surgeon with the option of not using the flanges at all.

In one embodiment, the flanges can be formed of titanium, such as malleable titanium. In this and other embodiments, the housing of the implantable component can also be formed from titanium. In another embodiment, the housing of the implantable component and/or the flanges can be formed of other materials, including suitable biocompatible metallic, ceramic and polymeric materials. In this regard, the flanges and housing do not need to be formed of the same material. For example, the flanges could be formed of a polymeric material, such as polypropylene or polytetrafluoroethylene, while the housing is formed of a ceramics or metallic material.

As defined above, the flanges are preferably securable to the surface of the tissue within the recipient. In one embodiment, one or more of the flanges can have orifices passing therethrough. These orifices can be adapted to receive tissue fixation devices, such as screws, clips and/or nails, including bone screws, bone clips and bone nails. In one embodiment, the screws can be countersunk, or have a round head. Still further, the tissue fixation devices can be resorbable.

In one embodiment, the housing is preferably adapted to be secured to the tissue surface at the site of each flange. It will, however, be appreciated that there may be instances where it is not possible to use a particular flange due to a previous cavity having been formed in the selected tissue, or, for example, the presence of a skull growth line, or a region of bone weakness.

In the above embodiments, the flanges and/or housing can be coated with a layer of silicone rubber or other suitable elastomeric material. The tissue fixation devices would preferably be accessible by means of a slit or hole formed or formable in the coating material.

According to a second aspect, the present invention is a medical implant for implantation within a body of a recipient, the medical implant comprising a hermetically sealed housing, said housing having at least one flange extending outwardly therefrom that is securable and conformable to tissue within the body of the recipient.

In this aspect, the said at least one flange can be formed of a malleable material. In this aspect, the implant, housing and flange can have any one or more of the features defined herein with reference to the first aspect.

In the case of a cochlear implant, an electrically conducting lead preferably extends from the receiver/stimulator package to an electrode array. The lead preferably exits the package such that it is extendable into the cochlea of the recipient on appropriate positioning of the implantable component within the recipient. In a preferred embodiment, the lead preferably extends from the implanted package to the cochlea via a posterior tympanotomy positioned at the bottom of a mastoid cavity. Other lead positions and geometries are can, however, be envisaged.

The present invention provides a housing of an implantable component having one or more flanges for use in securing the component to a tissue surface of the recipient. In addition to supporting the component, the flanges have the additional characteristic of serving to protect the component from inadvertent dislodgment following an impact that might otherwise dislodge the component if positioned and mounted using conventional techniques.

BRIEF DESCRIPTION OF THE DRAWINGS

By way of example only, a preferred embodiment of the invention is now described with reference to the accompanying drawings, in which:

FIGS. 6a and 6b are an end view and a side view, respectively, of the embodiment shown in FIG. 4 with the implant being sunk lower into the skull than that shown in FIG. 5a;

PREFERRED MODE OF CARRYING OUT THE INVENTION

Figure 1:
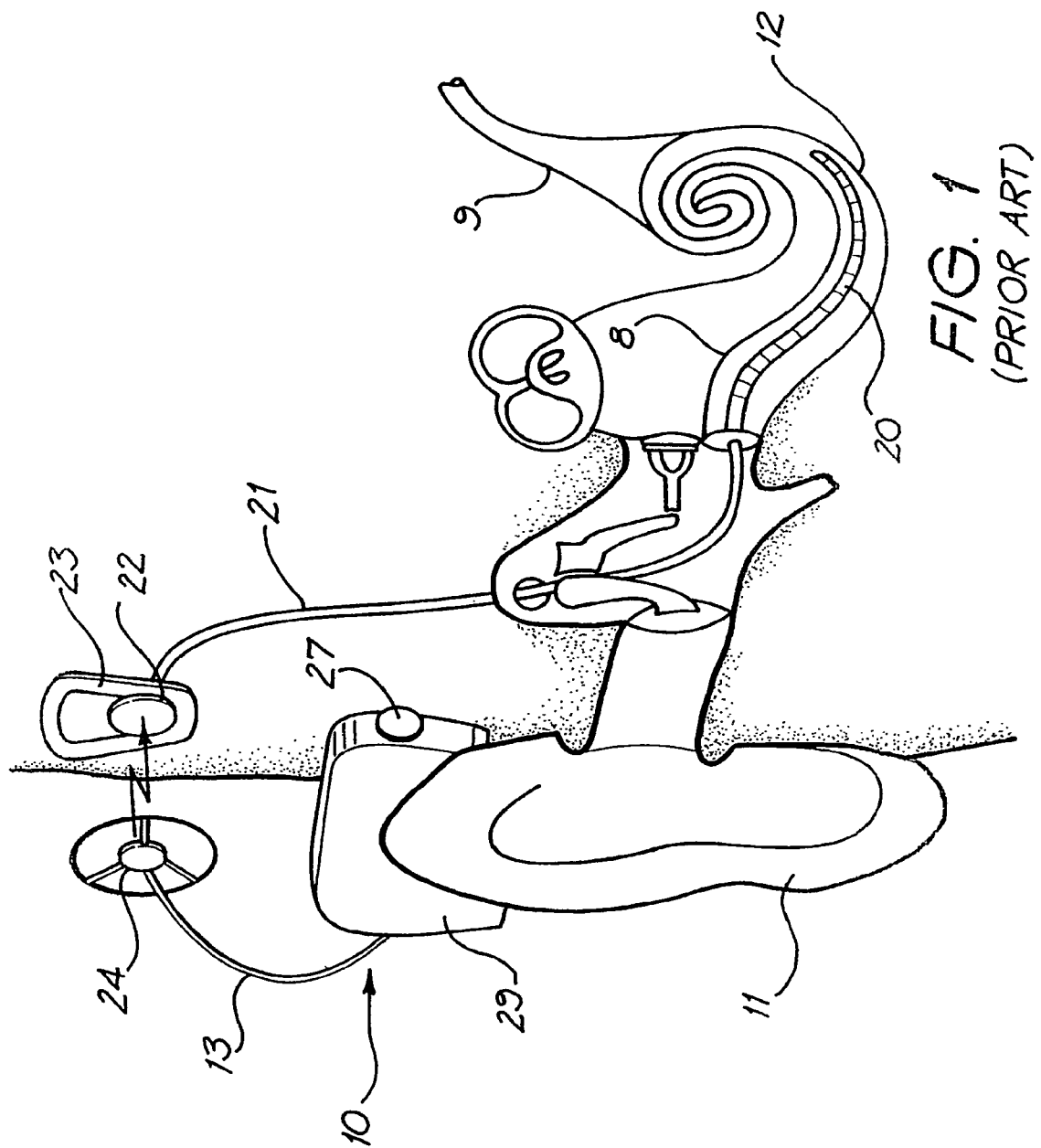
FIG. 1 is a pictorial representation of a conventional cochlear implant system.

Before describing the features of the present invention, it is appropriate to briefly describe the construction of one type of known cochlear implant system with reference to FIG. 1.

Known cochlear implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11 and is held in place behind the outer ear 11 via an ear-hook arrangement. Alternative versions may be worn on the body. Attached to the speech processor 29 via a cable 13 is a transmitter antenna coil 24 that transmits electrical signals to the implanted unit 22 via a radio frequency (RF) link.

The implanted component includes a receiver antenna coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930.

Figure 2:
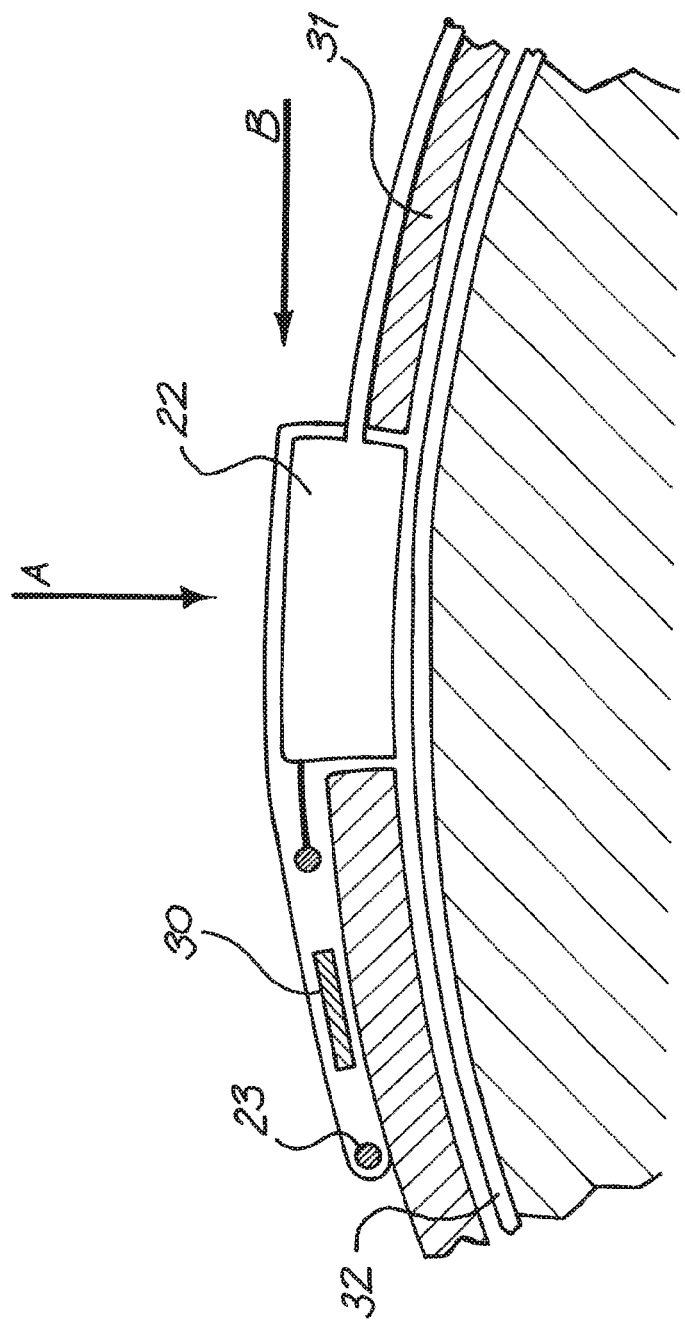
FIG. 2 is a representation of a conventional receiver/stimulator unit positioned in a bed fashioned in the mastoid bone according to conventional surgical techniques.

FIG. 2 shows in more detail the surgical placement of the implanted receiver and stimulator package 22 of FIG. 1, according to conventional practices. The package 22 is in the form of a capsule, for example a titanium capsule, which houses the necessary circuitry required for the implant to operate as desired. The receiver antenna coil 23 is shown encapsulated in a material, such as silicone rubber, to provide a protective body and ensure fatigue resilience. A magnet 30 is shown positioned within the coil to assist in the alignment of the transmitter coil 24 with the receiver antenna coil 23 as discussed previously. As is shown, a bed is drilled into the bone 31 to maintain the package 22 in position. This bed is typically round or ovoid to match the shape of the package. The bed is typically made in the mastoid bone and mastoid angle of the parietal bone in the region of the asterion. Typically, the bed is fashioned initially with a cutting burr, and then completed with a diamond paste burr and a template is typically used to ensure that the bed is fashioned to the correct size. As is shown, the bed may be drilled down to the lining of the brain, or dura mater 32, particularly for young children with thin skulls, and it is for this reason that a diamond paste burr may be used when approaching the dura and when the dura is exposed, to minimise the risk of tearing of the dura 32.

As can be appreciated from FIG. 2, any impact in the direction shown by the arrow A of FIG. 2, has the potential for the package to tear the dura 32 and enter the cranial cavity, potentially causing damage to the sensitive structures of the brain. Further to this, an impact to the head region of the recipient, particularly in the direction shown by arrow B, has the potential to dislodge the implant from its bed within the skull bone. Such dislodgment can cause damage to the area of the head adjacent the device as well as discomfort to the recipient. Any dislodgment of the device also has the potential to require further surgical procedures to relocate the device in the desired position within the head of the recipient. Further to this, such dislodgment of the device may cause the location of the strategically positioned electrodes of the electrode array to be altered, requiring possible re-implantation to rectify this problem.

Figure 3:
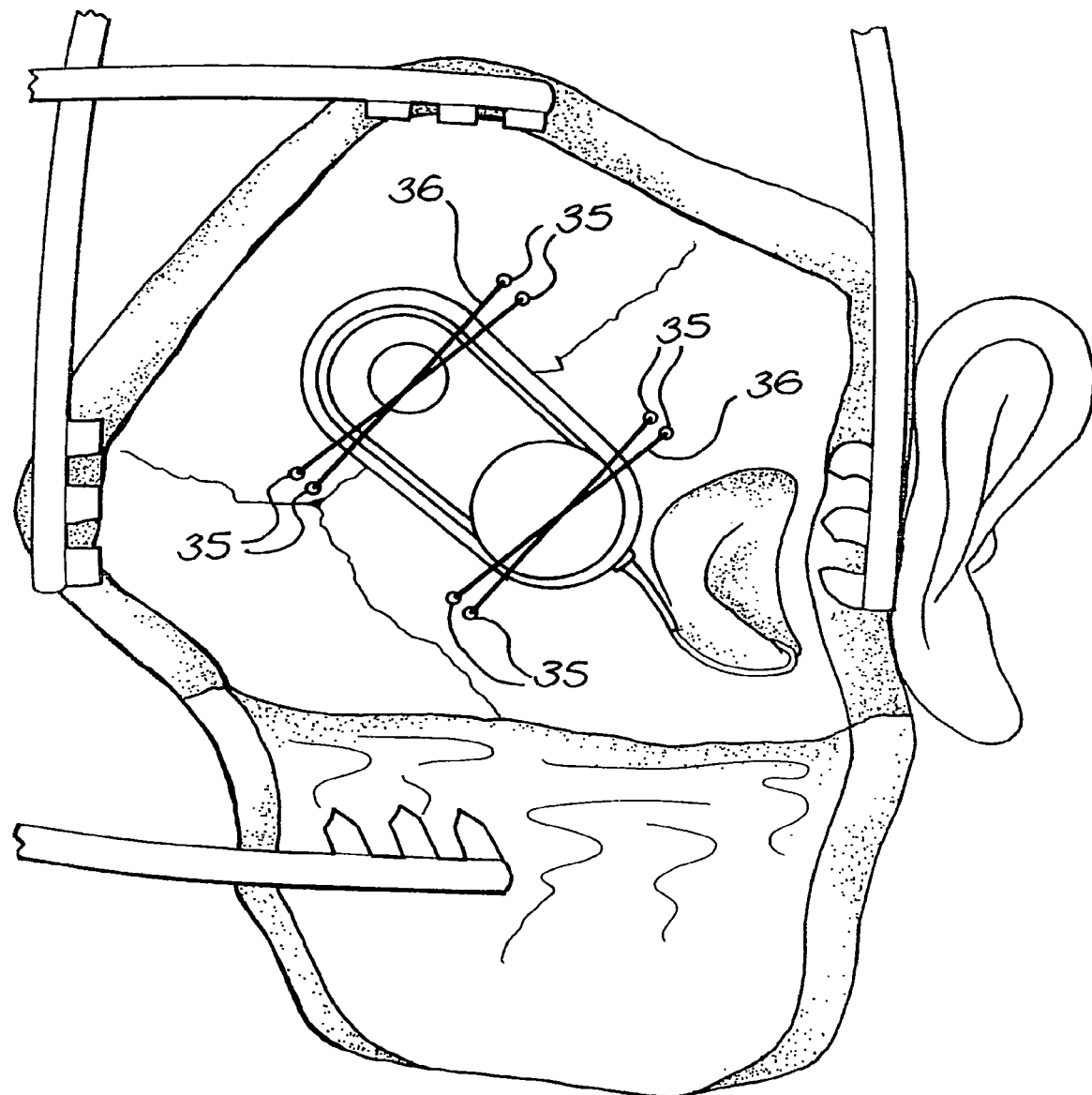
FIG. 3 is a representation of a typical prior art method of fixing the receiver/stimulator unit in place during surgery.

FIG. 3 depicts a typical fixation technique used to secure the device 22 in place prior to wound closure during a surgical procedure. In such a technique, prior to fixation of the device 22, small tunnels 35 are drilled in the bone on either side of the package bed to place ties or sutures 36 to hold the receiver/stimulator package in place. As previously mentioned, in an infant, such a procedure is not recommended, as the bone is thin and the drill may abrade the dura. For children, one method of securing the device in place is to tie the device down with ligatures placed through the temporalis and deep fascia, and to also stitch the anteriorly based facial flap over the package.

Figure 4:
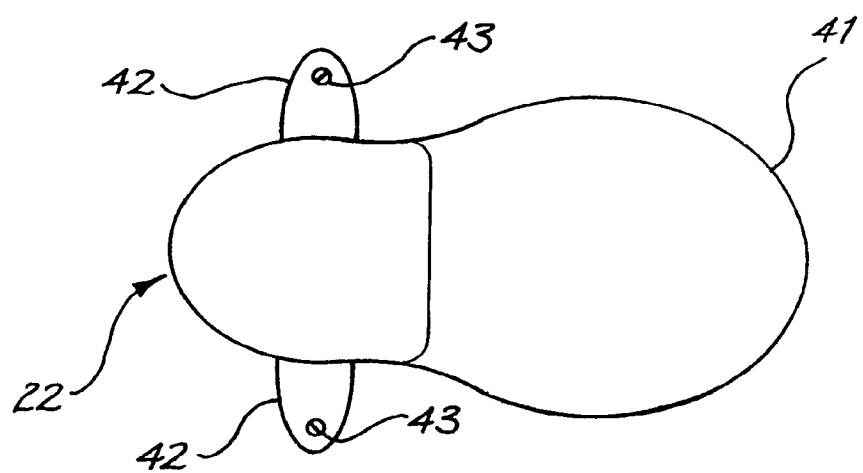
FIG. 4 is a plan view of one embodiment of the present invention.
Figure 5A:
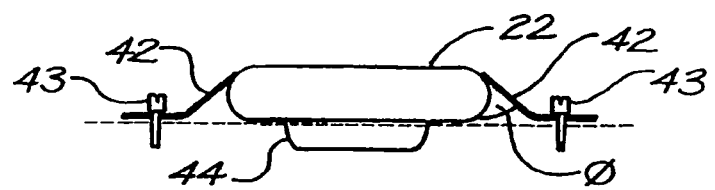
FIG. 5a is an end view of the embodiment shown in FIG. 4 mounted to a bone surface of a skull.
Figure 5B:
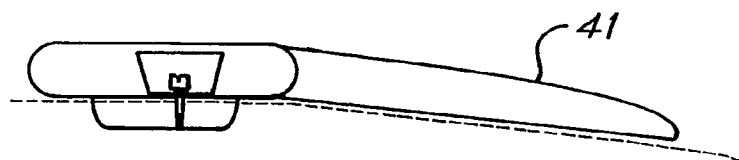
FIG. 5b is a side view of the embodiment shown in FIG. 4 mounted to a bone surface of a skull.

One embodiment of the fixation system according to the present invention is shown in FIGS. 4, 5a and 5b. In this embodiment, the implant package is once again shown by numeral 22, which preferably consists of a titanium casing enclosing the implant electronics. The silicone rubber material encapsulating the receiver coil is shown as 41, which in practice would encapsulate both the receiver antenna coil and a positioning magnet (not shown) as is known in the art. Two malleable flanges 42 are shown extending from the implant package 22. These malleable flanges 42 are suitably sized and shaped to be integrated with the implant package 22 so that the package 22 can be secured in place by securing the flanges to the skull via skull attachment devices 43 (ie. bone screws or pins). While depicted being securable to a bone surface, it will be appreciated that the present invention has application for mounting medical implants to other bodily tissues.

The malleable flanges 42 are preferably made from a titanium material and, in the depicted embodiment, are attached to the titanium implant package 22 by welding. Alternatively, the flanges 42 may be made integral with the implant package 22, and may merely be extension of the package 22. It is envisaged that other metals may be used for the implant package 22 and flanges 42, for example, any biocompatible metal such as stainless steel. It would, however, be preferable that the material used for the implant package 22 and/or flanges 42 be non-magnetic to allow MRI compatibility.

The skull attachment devices 43 are typically surgical screws and preferably have a low profile so they do not cause tissue erosion in the region of the head surrounding the implant, or produce a noticeable protuberance. Preferably, the flanges 42 and skull attachment devices 43 are coated in a silicone rubber to prevent tissue erosion, with the skull attachment devices 43 being accessed by means of a slit or hole in the silicone rubber above the skull attachment devices 43.

As shown in FIGS. 5a and 5b, the flanges 42 are attached to the uppermost surface of the implant package 22, with part of the implant package 22, hereby referred to as the implant pedestal 44, being sunk into the skull. In these figures, the dotted line represents the line of the skull. It should be appreciated that in all embodiments shown the pedestal 44 is not essential to the invention, and is only shown here to illustrate that the present invention is applicable to implants of variable configurations. It should also be appreciated that other such embodiments are possible and it is not necessary for the flanges 43 to be attached to the uppermost surface of the package 22, as the flanges 43 could be equally connected to other regions of the implant package 22.

As can be appreciated in FIGS. 5a and 5b, the flanges 43 must be sufficiently robust and yet sufficiently malleable to enable them to be formed and manipulated to fit the shape of the recipient's skull. As this manipulation typically occurs during the surgical implantation procedure, it is important that the forces required to manipulate the flanges 43 can be performed by the surgeon using finger pressure only. As the anatomy in this area of the head varies from patient to patient, it is desirable to form the flanges 43 so as to have a flush fit against the skull so as to maintain a low profile of the device and to reduce the occurrence of tissue erosion. In this regard, the flanges 43 would preferably only need to be manipulated to a relatively small degree.

Figure 6A:
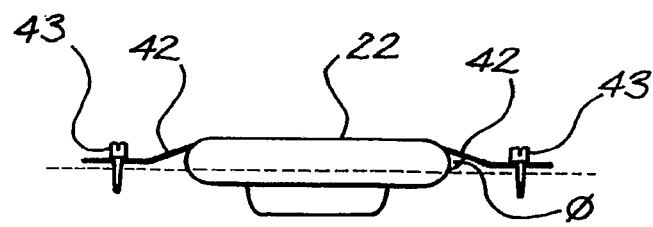
Figure 6B:
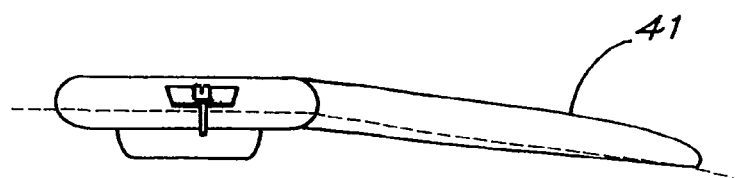

As surgical methods and preferences vary from surgeon to surgeon, it is important that the present invention can also be adapted to meet such variations. As can be seen in FIGS. 6a and 6b, some surgeons may prefer to partially sink the implant package 22 into the skull bone, with the dotted line in both figures representing the line of the skull. In such a case, the flanges 42 must be malleable to allow the surgeon to bend them to the correct position to suit the preferred depth of the implant bed or well. By a direct comparison between the implants depicted in FIGS. 5a and 5b and FIGS. 6a and 6b, it can be seen that in the case where the implant package is sunk to a deeper depth (FIGS. 6a and 6b), the angle ($\Phi$), the downward angle with which the flanges 42 exit the implant package 22, can be adjusted accordingly. The angle ($\Phi$) shown in FIGS. 6a and 6b has been increased to compensate for the greater depth of the implant bed than that shown in FIGS. 5a and 5b. This malleability characteristic can be achieved by selection of the material and/or thickness and/or geometry of the flanges 42. For example, annealed titanium of a thickness between 0.1-0.3 mm of the flange shape shown in FIG. 4, would be sufficiently malleable for a surgeon to bend during surgery.

Figure 7A:
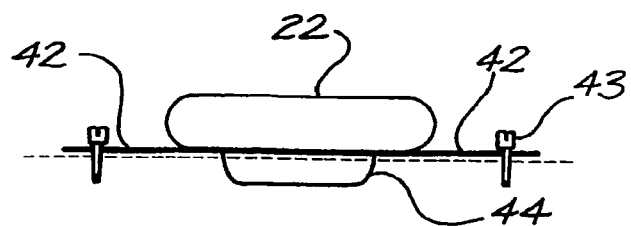
FIGS. 7a and 7b are an end view and a side view, respectively, of an alternative embodiment of the present invention.
Figure 7B:
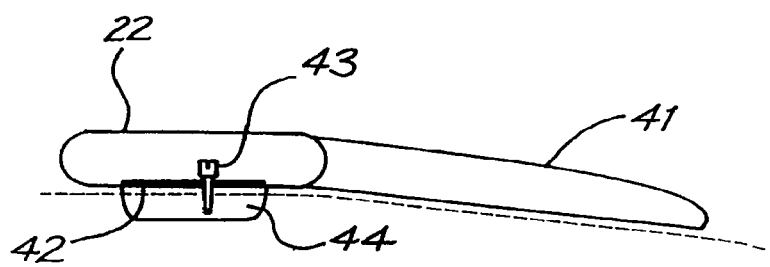

FIGS. 7a and 7b show an alternative embodiment of the present invention. In this embodiment, the malleable flanges 42 are arranged to exit the implant package 22 from a lower surface of the package, but with the implant pedestal 44 still adapted to be positioned within a well formed in the skull. In this embodiment, the flanges 42 would preferably lie flush with the skull, and such a design may be more preferable for younger children having thinner skin flaps over the implant.

Figure 7C:
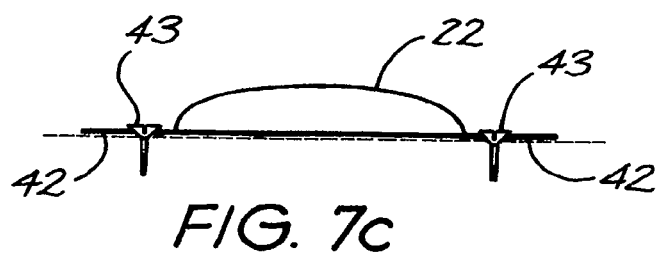
FIGS. 7c and 7d are an end view and a side view, respectively, of yet another alternative embodiment of the present invention.
Figure 7D:

FIGS. 7c and 7d show a further variation of the embodiment of FIGS. 7a and 7b. In this embodiment, the malleable flanges 42 are also arranged to exit the implant package 22 from the lower surface of the implant package. In this embodiment, there is no need to drill into the recipient's skull to form a bed for a pedestal 44 and the implant package can be quickly and securely fixed to the recipient's skull via skull attachment devices 43. In this embodiment, the implant package 22 is also provided with a domed profile to avoid the occurrence of tissue erosion.

Figure 8A:
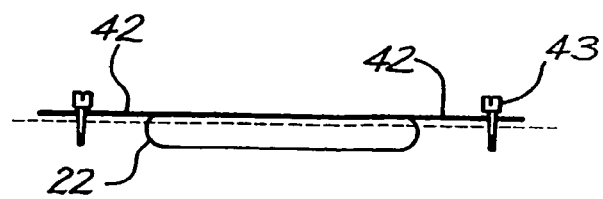
FIGS. 8a and 8b are an end view and a side view, respectively, of yet another embodiment of the present invention.
Figure 8B:
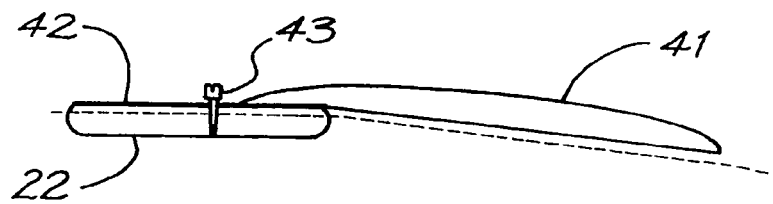

FIGS. 8a and 8b show yet another variation of the present invention. In this embodiment, the flanges 42 are attached to the uppermost surface of the implant package 22, with the implant package 22 positioned below the flanges 42. In this embodiment, a thin implant package can be sunk into the skull, ensuring that there is a minimal protuberance caused by the device.

Figure 9A:
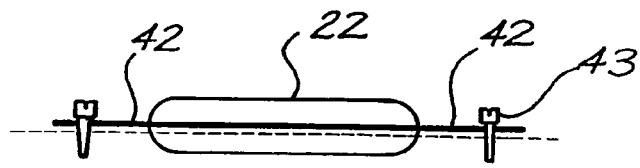
FIGS. 9a and 9b are an end view and a side view, respectively, of an alternative embodiment of the present invention.
Figure 9B:
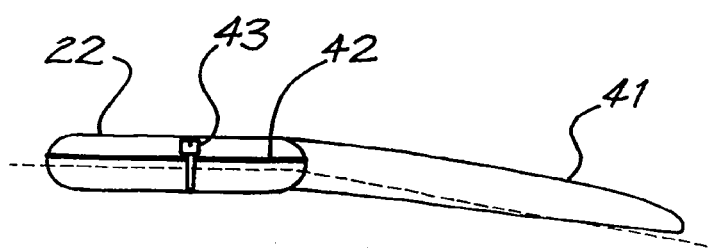
Figure 10:
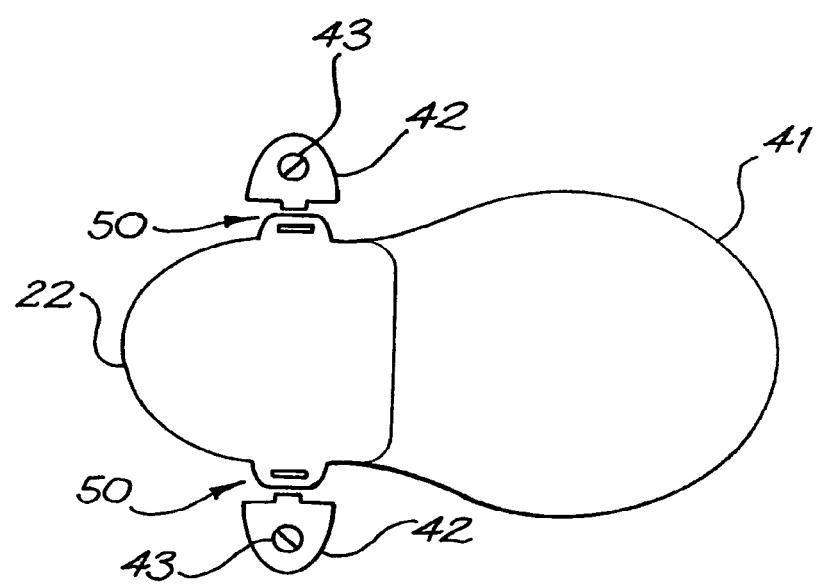
FIG. 10 is an alternative embodiment of the present invention having detachable flange portions.

FIGS. 9a and 9b depict yet another embodiment of the present invention where the flanges 42 are attached at about the mid-line of the implant package 22, with the implant package 22 being typically partly buried in the skull. In this embodiment, the flange 42 would also preferably be positioned flush with the skull, while the bed or well for the implant package would be fashioned in such a manner so as the antenna body is also partly sunk into the skull as shown. Such an embodiment does not require a pedestal 44 and ultimately provides a low profile implant that does not produce an unsightly protuberance and the problems associated therewith.

It should be appreciated that each of the flanges 42 shown in the above mentioned embodiments could be made from a plastic or elastomeric materials bonded to the implant package 22. For example, the silicone rubber coating of the implant package 22 can be extended to create a silicone rubber flange which may be secured to the skull via appropriate means. Further, a plastic material, such as PTFE or polyurethane, can be embedded within the silicone rubber coating of the implant package 22 to form a flange. Such a device may also be attached to the implant package via a mechanical interlock. It may also be possible to make the flange of a composite or combination of materials. For example, a Dacron mesh may be used as a reinforcing structure to strengthen the silicone rubber coating. PTFE, polyurethane or carbon fibre materials may also be used as a reinforcing member.

By providing the flange made from a plastic or elastomeric material, it then becomes possible for the surgeon to remove or cut-off the flange during the surgical procedure should they not wish to use such a fixation method. This results in the fixation mechanism being an optional feature. Such a flange would also be easier to form and alter the shape thereof to more appropriately conform to the shape of the recipient's skull. Further, a flange made from a plastic or elastomeric material is softer than a metallic flange and will therefore be less prone to causing tissue erosion.

FIGS. 10, 11a, 11b, 12a, and 12b depict yet another embodiment of the present invention. In this embodiment, the flanges 42 are detachable from the implant package 22. Each flange 42 is attached to the implant package 22 via lugs or clips 50 protruding from the side of the case of the implant package 22. The flanges 42 are received in the lugs or clips 50 and can be securely attached to the skull via appropriate skull attachment devices 43. This embodiment has the advantage that there is no need for a separate flange plate which adds thickness to the implant package. Further, the use of the flanges is optional, should the surgeon prefer not to use the flanges to secure the implant in place.

Figure 11A:
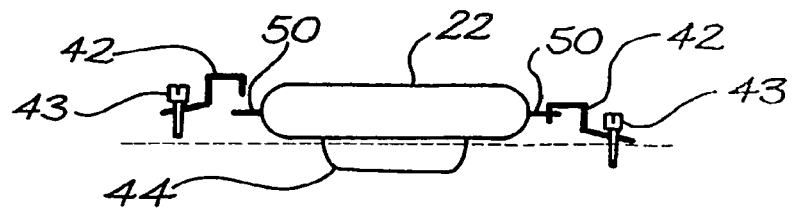
FIGS. 11a and 11b are an end view and a side view, respectively, of the embodiment shown in FIG. 10.
Figure 11B:
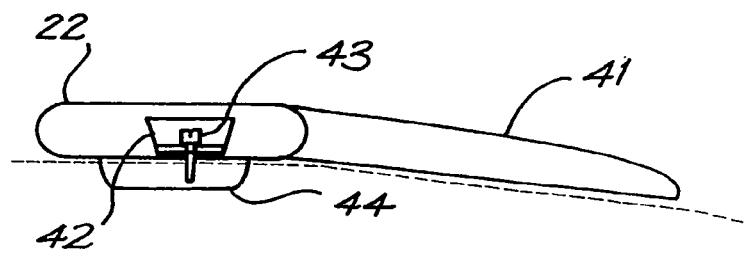
Figure 12A:
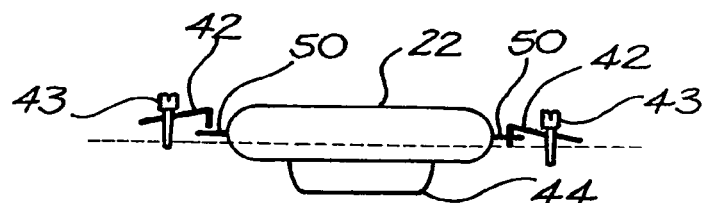
FIGS. 12a and 12b are an end view and a side view, respectively, of the embodiment shown in FIG. 10 where the implant has been sunk lower into the skull than that depicted in FIGS. 11a and 11b.
Figure 12B:
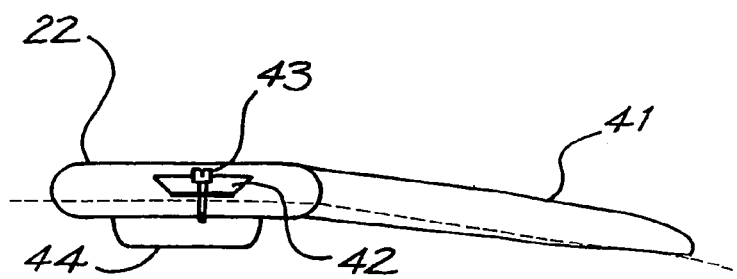

As is shown in FIGS. 11a, 11b, 12a and 12b, this embodiment allows the implant to be sunk into the skull to varying depths as decided by the surgeon during surgery. FIGS. 11a and 11b depict the implant positioned to a depth where only the pedestal 44 is sunk into the skull, with the detachable flanges 42 fixing the device in place through engagement with the lugs or clips 50 formed on the implant package 22. FIGS. 12a and 12b depict the implant being positioned deeper within the skull bone, with the detachable flanges 42 engaging with the lugs or clips 50 to secure the device in place.

Figure 13:
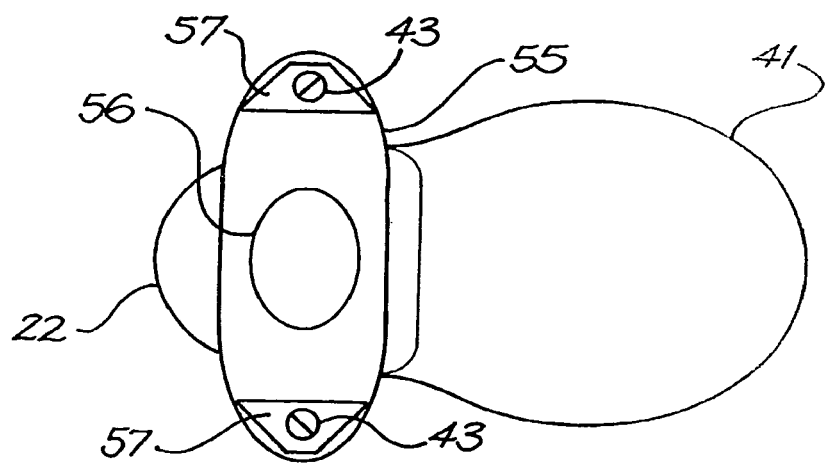
FIG. 13 is yet another embodiment of the present invention having a detachable flange plate.

FIG. 13 depicts yet another embodiment of the present invention. In this embodiment, a detachable flange plate 55 is used instead of separate flange elements that are integrally fixed or detachably fixed as shown in previous embodiments. The detachable flange plate 55 extends over and across the implant package 22, with skull attachment devices 43 being used to secure the plate 55 and therefore the implant package 22 in position. As is shown in FIG. 13, the plate 55 could include a cut-out section 56 should an electrode be positioned on the implant package casing 22 (as is the case with some currently existing implants) such that body fluids can access the electrode. There may also be a need to provide washers 57 to assist in securing the plate to the skull via the skull attachment devices, especially if a non-metallic plate is used. The plate 55 can be malleable to conform with the desired shape of the recipient's skull, and the shape can easily be manipulated by the surgeon during surgery.

Figure 14A:
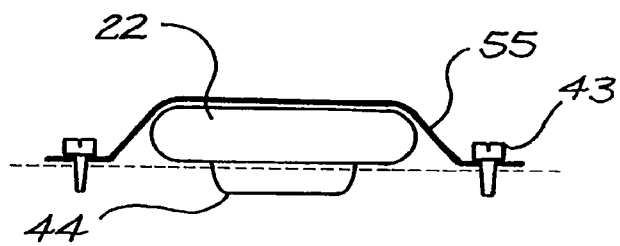
FIGS. 14a and 14b are an end view and a side view, respectively, of the embodiment shown in FIG. 13.
Figure 14B:
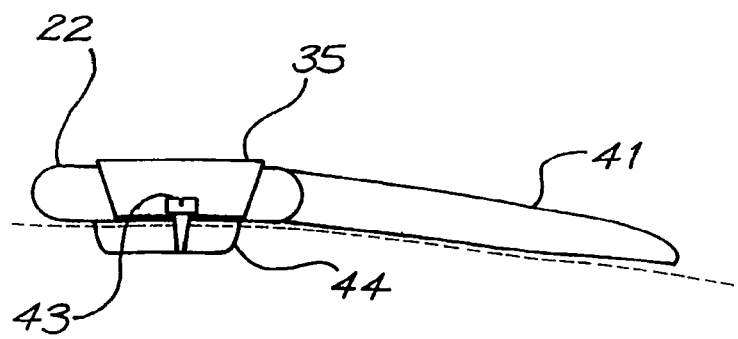

FIGS. 14a and 14b depicts the plate in use. As can be appreciated, the shape of the plate can be easily manipulated to cater for variable depths of implantation of the package 22 into the skull.

The embodiment as shown in FIG. 13 has advantages in that the plate 55 is an optional feature, and should a surgeon decide that such a method of fixation is not suitable for the patient during surgery, then the surgeon can choose not to use the plate 55. Further to this, the plate 55 could be used with existing implants without any need to modify the design of present implant packages to accommodate such a securing mechanism. This is important, particularly in the case of implants utilising a ceramic or non-metallic casing, as these implants do not allow for metal flanges to be welded to the non-metallic casing.

As alluded to above, the plate 55 may be made of a non-metallic material, such as a biocompatible plastic since there is no need for welding of the plate to the implant package 22. Such a plate would overcome the need to provide a coating of silicone rubber to the surface of the plate to soften it and prevent tissue erosion. In this regard, the plate 55 could be made of a polyurethane or PTFE which are strong, relatively inelastic materials suited to this application. However, it should be envisaged that other plastics may also be used which exhibit the desired properties.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:
1. A method, comprising:
obtaining access to a skull of a recipient;
placing a medical implant assembly into the recipient such that the medical implant assembly is in contact with the skull; and
placing a component over the medical implant assembly and screwing the component to the skull at at least one location to a side of the medical implant assembly such that the component holds the medical implant assembly to the skull, wherein the medical implant assembly includes a hermetically sealed housing, wherein the housing encases an electrical apparatus utilized to evoke a hearing percept in the recipient, the medical implant assembly includes a receiver coil and magnet assembly, the receiver coil and magnet assembly comprising a magnet and a receiver coil, the receiver coil and magnet assembly being located outside of the housing, and upon completion of the action of placing the component over the medical implant assembly, at least a portion of the housing is located below a surface of the skull at a border of a cavity in the skull and at least a portion of the receiver coil and magnet assembly is located above the surface of the skull.

2. The method of claim 1, wherein:
a downward force is applied to the housing as a result of the screwing action.

3. The method of claim 1, wherein:
the component is located entirely above the housing upon completion of the screwing action.

4. The method of claim 1, wherein:
the action of screwing the component to the skull includes placing screws at respective locations on either side of the medical implant assembly and screwing the screws into the skull at the respective locations.

5. The method of claim 4, wherein:
the component is completely on top of the medical implant assembly upon completion of screwing the screws into the skull.

6. The method of claim 1, further comprising:
determining whether or not to utilize the component, wherein
the component is an optional feature to be added to the medical implant assembly and the medical implant assembly is configured to be implanted in the recipient without the component holding the medical implant assembly to the skull.

7. The method of claim 1, wherein:
the component is a plate; and
the plate is spaced away from a top surface of the medical implant assembly.

8. The method of claim 1, wherein:
the component is a plate; and
the plate is a detachable plate relative to the housing.

9. The method of claim 1, wherein:
the skull is a skull in which the cavity has been prepared in the surface thereof; and
the action of placing the component over the medical implant assembly and screwing the component to the skull at at least one location to a side of the medical implant assembly results in the component holding at least a portion of the medical implant assembly at least partially in the cavity.

10. The method of claim 1, wherein:
the component includes two projections extending past outer boundaries of the medical implant assembly, the two projections being the only projections extending past outer boundaries of the medical implant assembly.

11. The method of claim 10, wherein:
the at least two projections are part of a single element that can be removed from contact with the medical implant assembly while the medical implant assembly remains hermetically sealed.

12. The method of claim 1, wherein:
the component has a side that has a surface area, which side faces away from the medical implant assembly after the component is screwed to the skull, the surface area of the side of the component being less than a surface area of the medical implant assembly of a side thereof facing the component after the component is screwed to the skull.

13. The method of claim 1, wherein:
the component is more than twice as long as it is wide.

14. The method of claim 1, wherein:
the housing includes an at least generally planar surface opposite the component across which the component completely extends, the at least generally planar surface being exposed to an ambient environment of the medical implant assembly when implanted in the skull.

15. The method of claim 1, wherein:
with respect to a view looking directly downward on the medical implant assembly along a lateral axis of the medical implant assembly, the component is above the medical implant assembly after the component is screwed to the skull, one side of the medical implant assembly has an outer profile that is semi-circular, and the component lies over a foci of the semi-circular profile.

16. The method of claim 1, wherein:
with respect to a view looking directly downward on the medical implant assembly along a lateral axis of the medical implant assembly, the medical implant assembly extends under the component from one side of the component to the opposite side of the component after the component is screwed to the skull, and with respect to that same view, the component extends over the medical implant assembly from one side of the medical implant assembly to the opposite side of the medical implant assembly.

17. The method of claim 1, wherein:
the action of placing the medical implant assembly into the recipient is executed by placing the medical implant assembly into a bed in the skull.

18. The method of claim 17, wherein:
the component is completely on top of the medical implant assembly upon completion of screwing the screws into the skull.

19. The method of claim 1, wherein:
the component is not a plate; and
the component is not spaced away from a top surface of the medical implant assembly.

20. The method of claim 1, wherein:
upon the completion of the method, the component and screws, and, if present, washers, are the only artificial structure holding the medical implant assembly in place.

21. A method, comprising:
obtaining access to a skull of a recipient;
placing a medical implant assembly into the recipient such that the medical implant assembly is in contact with the skull; and
placing a component over the medical implant assembly and screwing the component to the skull at at least one location to a side of the medical implant assembly such that the component holds the medical implant assembly to the skull, wherein
the medical implant assembly includes a hermetically sealed housing, wherein the housing encases an electrical apparatus utilized to evoke a hearing percept in the recipient,
the medical implant assembly includes a receiver coil and magnet assembly, the receiver coil and magnet assembly comprising a magnet and a receiver coil, the receiver coil and magnet assembly being located outside of the housing, and upon completion of the action of placing the component over the medical implant assembly, at least a portion of the housing is located below a surface of the skull at a border of a cavity in the skull and all of the receiver coil and magnet assembly is located above the surface of the skull.

22. The method of claim 21, wherein:
a downward force is applied to the housing as a result of the screwing action.

23. The method of claim 21, wherein:
the component is located entirely above the housing upon completion of the screwing action.

24. The method of claim 21, wherein:
the action of screwing the component to the skull includes placing screws at respective locations on either side of the medical implant assembly and screwing the screws into the skull at the respective locations.

25. The method of claim 24, wherein:
the component is completely on top of the medical implant assembly upon completion of screwing the screws into the skull.

26. The method of claim 21 further comprising:
determining whether or not to utilize the component, wherein
the component is an optional feature to be added to the medical implant assembly and the medical implant assembly is configured to be implanted in the recipient without the component holding the medical implant assembly to the skull.

27. The method of claim 21, wherein:
the component is a plate; and
the plate is spaced away from a top surface of the medical implant assembly.

28. The method of claim 21, wherein:
the component is a plate; and
the plate is a detachable plate relative to the housing.

29. The method of claim 21, wherein:
the skull is a skull in which the cavity has been prepared in the surface thereof; and
the action of placing the component over the medical implant assembly and screwing the component to the skull at at least one location to a side of the medical implant assembly results in the component holding at least a portion of the medical implant assembly at least partially in the cavity.

30. The method of claim 21, wherein:
the component includes two projections extending past outer boundaries of the medical implant assembly, the two projections being the only projections extending past outer boundaries of the medical implant assembly.

31. The medical implant of claim 30, wherein:
the at least two projections are part of a single element that can be removed from contact with the medical implant assembly while the medical implant assembly remains hermetically sealed.

32. The method of claim 21, wherein:
the component has a side that has a surface area, which side faces away from the medical implant assembly after the component is screwed to the skull, the surface area of the side of the component being less than a surface area of the medical implant assembly of a side thereof facing the component after the component is screwed to the skull.

33. The method of claim 21, wherein:
the component is more than twice as long as it is wide.

34. The method of 33, wherein:
the component is completely on top of the medical implant assembly upon completion of screwing the screws into the skull.

35. The method of claim 21, wherein:
the housing includes an at least generally planar surface opposite the component across which the component completely extends, the at least generally planar surface being exposed to an ambient environment of the medical implant assembly when implanted in the skull.

36. The method of claim 21, wherein:
with respect to a view looking directly downward on the medical implant assembly along a lateral axis of the medical implant assembly, the component is above the medical implant assembly after the component is screwed to the skull, one side of the medical implant assembly has an outer profile that is semi-circular, and the component lies over a foci of the semi-circular profile.

37. The method of claim 21, wherein:
with respect to a view looking directly downward on the medical implant assembly along a lateral axis of the medical implant assembly, the medical implant assembly extends under the component from one side of the component to the opposite side of the component after the component is screwed to the skull, and with respect to that same view, the component extends over the medical implant assembly from one side of the medical implant assembly to the opposite side of the medical implant assembly.

38. The method of claim 21, wherein:
the action of placing the medical implant assembly into the recipient is executed by placing the medical implant assembly into a bed in the skull.

39. The method of claim 21, wherein:
the component is not a plate; and
the component is not spaced away from a top surface of the medical implant assembly.

40. The method of claim 21, wherein:
upon the completion of the method, the component and screws, and, if present, washers, are the only artificial structure holding the medical implant assembly in place.

* * * * *